United States Patent [19]
Sanderson et al.

[11] Patent Number: 5,401,889
[45] Date of Patent: Mar. 28, 1995

[54] PREPARATION OF TERTIARY BUTYL ALCOHOL BY CATALYTIC DECOMPOSITION OF TERTIARY BUTYL HYDROPEROXIDE

[75] Inventors: John R. Sanderson, Leander; Mark A. Mueller, Austin, both of Tex.; Yu-Hwa E. Sheu, Hsinchu, Taiwan, Prov. of China

[73] Assignee: Texaco Chemical Inc., White Plains, N.Y.

[21] Appl. No.: 150,916

[22] Filed: Nov. 12, 1993

[51] Int. Cl.$^6$ .................. C07C 29/00; C07C 31/12; C07C 29/88
[52] U.S. Cl. .................. 568/909.8; 568/922
[58] Field of Search .................. 568/909.8

[56] References Cited

U.S. PATENT DOCUMENTS

| | | | |
|---|---|---|---|
| 3,505,360 | 4/1970 | Allison et al. | 569/909.8 |
| 3,591,656 | 7/1971 | Krell | 568/894 |
| 3,915,893 | 10/1975 | Flanigen et al. | 568/894 |
| 4,910,349 | 3/1990 | Sanderson et al. | 568/909.8 |
| 5,243,101 | 9/1993 | Sanderson et al. | 568/909.8 |

Primary Examiner—Joseph E. Evans
Attorney, Agent, or Firm—Kenneth R. Priem; James L. Bailey; Carl G. Ries

[57] ABSTRACT

A method for preparing tertiary butyl alcohol wherein a feedstock comprising a solution of tertiary butyl hydroperoxide in a cosolvent mixture of tertiary butyl alcohol with isobutane is charged to a hydroperoxide decomposition reaction zone containing a catalytically effective amount of a hydroperoxide decomposition catalyst and is brought into contact with the catalyst in liquid phase with agitation under hydroperoxide decomposition reaction conditions to convert the tertiary butyl hydroperoxide to decomposition products, principally tertiary butyl alcohol.

4 Claims, No Drawings

PREPARATION OF TERTIARY BUTYL ALCOHOL BY CATALYTIC DECOMPOSITION OF TERTIARY BUTYL HYDROPEROXIDE

BACKGROUND OF THE INVENTION

1. Field of the Invention

This invention relates to a method for the preparation of tertiary butyl alcohol (TBA) by the catalytic decomposition of tertiary butyl hydroperoxide (TBHP). More particularly, this invention relates to a method wherein a tertiary butyl hydroperoxide charge stock comprising a solution of tertiary butyl hydroperoxide dissolved in a cosolvent mixture of isobutane and tertiary butyl alcohol is brought into contact with a hydroperoxide decomposition catalyst in a reaction zone to convert the tertiary butyl hydroperoxide to peroxide decomposition products, principally tertiary butyl alcohol.

2. Prior Art

It is known to react isobutane with oxygen, either thermally or catalytically, to form a peroxidation reaction product wherein the principal peroxide that is formed is tertiary butyl hydroperoxide. It is also known to thermally or catalytically decompose the tertiary butyl hydroperoxide in a peroxide decomposition zone to form tertiary butyl alcohol. Normally, the unreacted isobutane is removed from the peroxidation reaction product so that the feedstock for the hydroperoxide decomposition zone is a debutanized peroxidation reaction product.

In the text entitled "Organic Peroxides" edited by Daniel Swern (Wiley Interscience, a Division of John Wiley & Sons, New York), in Vol. II on page 157 it is stated that the metal-ion-catalyzed decomposition of primary hydroperoxides yields mainly alcohols, aldehydes and carboxylic acids, citing as an example the decomposition of hydroxymethyl hydroperoxide with aqueous ferrous sulfate to provide formaldehyde, formic acid and water.

Quin U.S. Pat. No. 2,854,487 discloses the hydrogenation of hydrocarbon peroxides in the presence of hydrogen and palladium on activated alumina to provide carbinols.

In Massie U. S. Pat. No. 3,775,472 a process is disclosed wherein alkyl substituted aromatic hydrocarbons are oxidized to products such as aromatic alcohols, aldehydes and carboxylic acids in the presence of ruthenium compounds.

Grane U.S. Pat. No. 3,474,151 discloses that tertiary butyl alcohol starts to dehydrate at 450° F. and to decompose at a "rapid rate" at temperatures above 475° F. Grane discovered, however, that residual quantities of hydroperoxide contaminants present in tertiary butyl alcohol could be thermally decomposed by heating the contaminated tertiary butyl alcohol at a temperature of 375° to 475° F. for about 1 to 10 minutes.

Grane et al. U. S. Pat. No. 4,294,999 discloses a process wherein isobutane is oxidized in a pressured reactor in the presence of a solubilized molybdenum catalyst to provide a mixture of tertiary butyl alcohol, tertiary butyl hydroperoxide, methanol, acetone, and other oxygen-containing compounds. The tertiary butyl hydroperoxide is thermally decomposed under pressure at about 280° F. to provide a tertiary butyl alcohol product containing only residual quantities of tertiary butyl hydroperoxide which are then decomposed in accordance with Grane U.S. Pat. No. 3,474,151 by heating the tertiary butyl alcohol at 375° to 475° for about 1 to 10 minutes. Heating tertiary butyl alcohol containing small amounts of peroxides at high temperatures for even short periods of time to remove the peroxides produces undesirable products such as isobutylene.

Grane et al. U.S. Pat. No. 4,296,262 discloses a related process wherein isobutane is reacted with oxygen in a reaction zone for a residence time of about 1 to 10 hours at a temperature of about 240° to about 340° F. and a pressure of about 100 to about 1000 psig. in the presence of a catalytically effective amount of a soluble molybdenum catalyst. A liquid stream comprising tertiary butyl alcohol is recovered from the reaction mixture and fed to a decomposition zone wherein the tertiary butyl hydroperoxide contained therein is decomposed by "hot aging" at 250°–350° F. at a pressure lower than the pressure in the oxidation zone. The tertiary butyl alcohol can be further subjected to a clean-up treatment at 375°–475° F. for 1 to 10 minutes. Worrell et al. in U.S. Pat. No. 4,296,263 disclose a related process wherein the feedstock is a mixture of normal butane with isobutane and wherein the oxidation catalyst is a soluble form of chromium, cobalt, nickel, manganese, molybdenum, or a mixture thereof.

BACKGROUND INFORMATION

In U. S. Pat. No. 3,505,360, Allison et al. disclose a method wherein an alkenyl hydroperoxide is decomposed in the presence of a catalyst based on a compound of a Group IV-A, V-A or VI-A metal. Taylor et al., in U.S. Pat. No. 4,508,923 disclose the use of a catalyst system comprising ruthenium and chromium for decomposing organic hydroperoxides. The use of a cobalt borate catalyst for the decomposition of hydroperoxides is disclosed in Sanderson et al. U.S. Pat. No. 4,547,598.

Taylor et al. U.S. Pat. No. 4,551,553 is directed to a process for the formation of alcohols such as tertiary butyl alcohol by the catalytic decomposition of an organic hydroperoxide such as tertiary butyl hydroperoxide using a binary catalyst composed of a mixture of a ruthenium compound with a chromium compound. It is stated that the use of the binary catalyst eliminates the need for stabilizing ligands.

Sanderson et al. disclose the use of a variety of catalysts for the decomposition of tertiary butyl hydroperoxide in a series of U.S. patents, including a catalyst composed of unsupported nickel, copper, chromia and iron (U.S. Pat. No. 4,704,482), a catalyst composed of iron, copper, chromia and cobalt (U.S. Pat. No. 4,705,903), a catalyst composed of a base treated hydrogenation catalyst from groups VIB or VIIIB of the Periodic Table (U.S. Pat. No. 4,742,179), a catalyst consisting essentially of nickel, copper, chromium and barium (U.S. Pat. No. 4,873,380), a catalyst composed of a metal phthalocyanine promoted with a rhenium compound (U.S. Pat. No. 4,910,349), a catalyst composed of a base promoted metal phthalocyanine compound (U.S. Pat. No. 4,912,269), a catalyst composed of a soluble ruthenium compound promoted with a bidentate ligand (U.S. Pat. No. 4,912,033), a catalyst composed of a metal porphine such as iron (III) or manganese (III) promoted with an alkyl thiol or an amine, a catalyst composed of an imidazole promoted metal phthalocyanine compound (U.S. Pat. No. 4,912,266), (U.S. Pat. No. 4,922,034), a catalyst composed of a metal phthalocyanine promoted with a thiol and a free radical inhibitor (U.S. Pat. No. 4,922,035), a catalyst composed of a borate promoted metal phthalocyanine (U.S. Pat. No. 4,922,036), or a catalyst composed of a soluble ruthenium compound and an iron compound such as an acetate, a borate, a bromide, a chloride, a 1,3-propanedionate, a 2-ethylhexanoate, an iodide, a nitrate, a 2,4-pentanedionate, a perchlorate or a sulfate (U. S. Pat. No. 5,025,113).

When isobutane is reacted with molecular oxygen, the principal products of the reaction are tertiary butyl alcohol and tertiary butyl hydroperoxide. However, minor amounts of other contaminants are also formed.

In addition, a minor amount of water will be formed, which will normally amount to about 0.5 to 1 wt. % of the reactor effluent. The amount of byproduct water that is produced is a function of the severity of the reaction conditions employed and will tend to increase as the severity of the reaction conditions is increased.

As indicated, tertiary butyl hydroperoxide is useful as a raw material for the manufacture of tertiary butyl alcohol. The tertiary butyl alcohol can be formed by catalytic decomposition of the tertiary butyl hydroperoxide. In the Williams et al. process disclosed in U.S. Pat. No. 3,472,876, an oxygen-containing gas was charged to a reactor containing isobutane and an oxidation catalyst to provide a reaction mixture comprising tertiary butyl alcohol, tertiary butyl hydroperoxide, acetone, and tertiary butyl ether. The reported results in the patent indicate that there was comparatively low rate of conversion and a comparatively poor selectivity of the reaction to tertiary butyl alcohol.

SUMMARY OF THE INVENTION

In accordance with the present invention, a tertiary butyl hydroperoxide charge stock is used which comprises a solution of tertiary butyl hydroperoxide in a cosolvent mixture of isobutane with tertiary butyl alcohol.

A feedstock for the present invention is suitably one formed by the oxidation of isobutane with molecular oxygen to provide an oxidation reaction product containing a solution of tertiary butyl hydroperoxide in tertiary butyl alcohol and unreacted isobutane.

The tertiary butyl hydroperoxide charge stock will suitably comprise from about 5 to 30 wt. % of tertiary butyl hydroperoxide and, correspondingly, about 95 to 70 wt. % of cosolvent. The cosolvent will suitably comprise from about 50 to 80 wt. % of isobutane and, correspondingly, from about 50 to 20 wt. % of tertiary butyl alcohol. If the tertiary butyl hydroperoxide charge stock is an isobutane peroxidation reaction product that contains more than about 30 wt. % of tertiary butyl hydroperoxide, tertiary butyl alcohol may be added in amount sufficient to provide for the desired concentration of tertiary butyl hydroperoxide in the cosolvent mixture of isobutane and tertiary butyl alcohol.

The tertiary butyl hydroperoxide charge stock is charged to a catalytic hydroperoxide decomposition zone wherein the tertiary butyl hydroperoxide is decomposed in the presence of a suitable peroxide decomposition catalyst such as a palladium catalyst.

The tertiary butyl alcohol will not be the only decomposition product that is formed. Minor amounts of other oxygen-containing materials such as those listed above will also be formed.

The tertiary butyl alcohol that is recovered from the decomposition reaction mixture will be contaminated with the oxygenated impurities.

The Catalyst System

The catalyst system to be used in accordance with the present invention is a hydroperoxide decomposition catalyst. Any suitable peroxide decomposition catalyst may be used, such as a nickel, copper, chromia, iron catalyst of the type disclosed in Sanderson et al. U.S. Pat. No. 4,704,482, an iron, copper, chromia, cobalt catalyst of the type disclosed in Sanderson et al. U.S. Pat. No. 4,705,903, a nickel, copper, chromium and barium catalyst of the type disclosed in Sanderson et al. U.S. Pat. No. 4,873,380, a metal phthalocyanine catalyst of the type disclosed in Sanderson et al. U.S. Pat. No. 4,910,3349, or Sanderson et al. U.S. Pat. No. 4,912,269, or Sanderson et al. U. S. Pat. No. 4,922,035 or Sanderson et al. U.S. Pat. No. 4,922,036, a ruthenium catalyst of the type disclosed in Sanderson et al. U.S. Pat. No. 4,912,033, or Sanderson et al. U.S. Pat. No. 5,025,113, a palladium catalyst, such as a catalyst comprising about 0.1 to 1 wt. % of palladium supported on alumina and diluted, if desired, with about 100 wt. % to 500 wt. % of titania or zirconia, etc.

Catalytic Decomposition of Tertiary Butyl Hydroperoxide

The process of the present invention may be conducted batchwise in kettles or by continuously passing the reactants through a tubular reactor.

The catalytic decomposition of the tertiary butyl hydroperoxide is preferably conducted at a temperature within the range of about 25° to about 250° C. and, more preferably, at a temperature within the range of about 40° to about 150° C. The reaction is preferably conducted at a pressure sufficient to keep the products and reactants in liquid phase. Pressures, including autogenous pressure of about 0 up to about 10,000 psig. may be used, if desired.

Flow rates of the charge solution to the reaction zone should be adjusted in order to provide an appropriate contact time within the reactor. In a batch process, the holding time may suitably be from about 0.5 to about 10 hours, and more preferably about 1 to 3 hours. In a continuous process, the space velocity is suitably within the range of about 0.5 to 2 volumes of tertiary butyl hydroperoxide charge stock per volume of pelleted catalyst per hour.

In accordance with a preferred embodiment of the present invention, isobutane is reacted with oxygen in an oxidation zone under oxidation reaction conditions including a temperature of about 135° to about 155° C., a pressure of about 300 to about 800 psig., and a holding time of about 2 to about 6 hours to provide an initial oxidation reaction product comprising unreacted isobutane, tertiary butyl hydroperoxide, tertiary butyl alcohol, and oxygen-containing by-products. The initial oxidation reaction product is then used as the tertiary butyl hydroperoxide charge stock of the present invention. If the concentration of tertiary butyl hydroperoxide in the tertiary butyl hydroperoxide charge stock is more than about 30 wt. % of the initial oxidation reaction product, the initial oxidation reaction product can be diluted with an amount of tertiary butyl alcohol sufficient to lower the concentration of the tertiary butyl hydroperoxide to a desired percentage, to provide, for example, a tertiary butyl hydroperoxide charge stock containing from about 5 to about 25 wt. % of tertiary butyl hydroperoxide.

The remainder of the tertiary butyl hydroperoxide charge stock will comprise a mixture of isobutane and tertiary butyl alcohol, such as a mixture comprising about 20 to 50 wt. % of tertiary butyl alcohol with, correspondingly, about 80 to 50 wt. % of isobutane.

The tertiary butyl hydroperoxide charge stock is then charged to a catalytic hydroperoxide decomposition zone where it is brought into contact with a suitable hydroperoxide decomposition catalyst to convert the tertiary butyl hydroperoxide to tertiary butyl alcohol with high yield and selectivity.

When the process of the present invention is practiced in a continuous manner by continuously charging the tertiary butyl hydroperoxide charge stock to a reactor containing a fixed bed of pelleted hydroperoxide decomposition catalyst, the space velocity is suitably in the range of about 0.5 to about 3 volumes of tertiary butyl hydroperoxide charge stock per volume of catalyst per hour. Preferably, the space velocity is within the range of about 0.5 to about 1 volume of tertiary butyl hydroperoxide charge stock per volume of catalyst per hour.

The reaction product from the tertiary butyl hydroperoxide decomposition step may then be fractionated in any suitable manner, such as by distillation to recover the tertiary butyl alcohol.

SPECIFIC EXAMPLES

The invention will be further illustrated by the following specific examples which are given by way of illustration and not as limitations on the scope of this invention.

Reactor

The reactor was a stainless steel tube (0.51"×29") which was electrically heated. Liquid feed was pumped into the bottom of the reactor. Pressure regulation was with a Skinner Uni-Flow valve and a Foxboro controller. The liquid feed was pumped with a Ruska dual drive pump. Samples were collected at each space velocity and temperature using a 150 cc stainless steel bomb. The bomb was fitted with a pressure gage and rupture disk.

Isobutane peroxidation reactor effluent was obtained from a pilot plant peroxidation reactor.

Analysis of the reactor effluent was by GC. Details are given in the following tables.

TABLE I

CATALYTIC CONVERSION OF TERT-BUTYLHYDROPEROXIDE TO TERT-BUTYLALCOHOL

| Notebook Number | 7012-25-F | 7012-25-1 | 7012-25-2 | 7012-25-3 | 7012-25-4 |
|---|---|---|---|---|---|
| Catalyst | | .2% Pd, .08% Au on $Al_2O_3$ | | | |
| Catalyst (cc) | | 100 | 100 | 100 | 100 |
| Pressure (psig) | | 300 | 300 | 300 | 300 |
| Feed Rate (cc/Hr.) | | 50 | 50 | 50 | 50 |
| Temperature (°C.) | | 40 | 60 | 80 | 100 |
| Time on Stream (Hr) | | 4 | 4 | 4 | 4 |
| Space Vel. (cc/cc) | | 0.5 | 0.5 | 0.5 | 0.5 |
| TBHP Conversion (mol. %) | | 56.3 | 82.7 | 92.9 | 99.6 |
| IB Conversion (mol. %) | | 13.1 | 0.0 | 13.4 | 3.5 |
| Sel. Acetone (mol. %) | | 0.2 | 2.3 | 6.9 | 6.8 |
| Sel. Methanol (mol. %) | | 0.0 | 0.2 | 0.7 | 0.5 |
| Sel. TBA (mol. %) | | 99.8 | 91.7 | 86.9 | 89.5 |
| Sel. DTBP (mol. %) | | 0.0 | 6.1 | 6.1 | 3.7 |
| Composition | | | | | |
| C3= | 0.019 | 0.020 | 0.023 | 0.029 | 0.029 |
| Isobutane | 57.704 | 50.167 | 58.187 | 49.961 | 55.712 |
| MEOH/MF | 0.101 | 0.089 | 0.112 | 0.142 | 0.136 |
| Acetone | 1.128 | 1.139 | 1.346 | 1.875 | 1.915 |
| TBA | 21.338 | 38.448 | 34.791 | 43.904 | 40.044 |
| DTBP | 0.681 | 0.404 | 1.418 | 1.518 | 1.220 |
| TBHP | 18.084 | 7.894 | 3.126 | 1.291 | 0.079 |

If one compares Tables I–IV with Tables V–VII, it is clear that the selectivities to TBHP are higher in the presence of isobutane. This is at least partially due to the conversion of a portion of the isobutane to TBA.

TABLE II

CATALYTIC CONVERSION OF TERT-BUTYLHYDROPEROXIDE TO TERT-BUTYLALCOHOL

| Notebook Number | 7012-25-F | 7012-25-5 | 7012-25-6 | 7012-25-7 | 7012-25-8 |
|---|---|---|---|---|---|
| Catalyst | | .2% Pd, .08% Au on $Al_2O_3$ | | | |
| Catalyst (cc) | | 100 | 100 | 100 | 100 |
| Pressure (psig) | | 300 | 300 | 300 | 300 |
| Feed Rate (cc/Hr.) | | 50 | 50 | 50 | 50 |
| Temperature (°C.) | | 40 | 60 | 80 | 100 |
| Time on Stream (Hr) | | 4 | 4 | 4 | 4 |
| Space Vel. (cc/cc) | | 0.5 | 0.5 | 0.5 | 0.5 |
| TBHP Conversion (mol. %) | | 21.7 | 62.9 | 87.8 | 96.5 |
| IB Conversion (mol. %) | | 1.2 | n.d. | 0.3 | 7.5 |
| Sel. Acetone (mol. %) | | 2.5 | 1.9 | 4.7 | 7.6 |
| Sel. Methanol (mol. %) | | 0.5 | 0.2 | 0.5 | 1.0 |
| Sel. TBA (mol. %) | | 88.4 | 92.1 | 90.6 | 88.1 |
| Sel. DTBP (mol. %) | | 9.1 | 6.0 | 4.7 | 4.3 |
| Composition | | | | | |
| Isobutane | 57.704 | 56.992 | 59.018 | 57.534 | 53.360 |
| MEOH/MF | 0.101 | 0.108 | 0.110 | 0.131 | 0.163 |
| Acetone | 1.128 | 1.191 | 1.265 | 1.605 | 1.988 |
| TBA | 21.338 | 25.640 | 30.712 | 36.183 | 41.556 |
| DTBP | 0.681 | 0.971 | 1.237 | 1.291 | 1.285 |

TABLE II-continued

CATALYTIC CONVERSION OF TERT-BUTYLHYDROPEROXIDE TO TERT-BUTYLALCOHOL

| Notebook Number | 7012-25-F | 7012-25-5 | 7012-25-6 | 7012-25-7 | 7012-25-8 |
|---|---|---|---|---|---|
| TBHP | 18.084 | 14.165 | 6.709 | 2.198 | 0.631 |

TABLE III

CATALYTIC CONVERSION OF TERT-BUTYLHYDROPEROXIDE TO TERT-BUTYLALCOHOL

| Notebook Number | 7012-25-F | 7012-26-1 | 7012-26-2 | 7012-26-3 | 7012-26-4 |
|---|---|---|---|---|---|
| Catalyst | | .2% Pd, .08% Au on $Al_2O_3$ | | | |
| Catalyst (cc) | | 100 | 100 | 100 | 100 |
| Pressure (psig) | | 300 | 300 | 300 | 300 |
| Feed Rate (cc/Hr.) | | 100 | 100 | 100 | 100 |
| Temperature (°C.) | | 40 | 60 | 80 | 100 |
| Time on Stream (Hr) | | 4 | 4 | 4 | 4 |
| Space Vel. (cc/cc) | | 1.0 | 1.0 | 1.0 | 1.0 |
| TBHP Conversion (mol. %) | | 4.9 | 56.0 | 83.2 | 95.7 |
| IB Conversion (mol. %) | | n.d. | n.d. | 11.0 | 12.9 |
| Sel. Acetone (mol. %) | | n.d. | 1.6 | 6.9 | 11.3 |
| Sel. Methanol (mol. %) | | n.d. | 0.1 | 4.7 | 6.1 |
| Sel. TBA (mol. %) | | n.d. | 93.0 | 88.0 | 85.2 |
| Sel. DTBP (mol. %) | | n.d. | 5.4 | 5.0 | 3.5 |
| Composition | | | | | |
| Isobutane | 57.704 | 58.610 | 60.017 | 51.337 | 50.249 |
| MEOH/MF | 0.101 | 0.099 | 0.106 | 0.351 | 0.477 |
| Acetone | 1.128 | 1.077 | 1.232 | 1.801 | 2.386 |
| TBA | 21.338 | 21.354 | 28.601 | 40.571 | 43.475 |
| DTBP | 0.681 | 0.714 | 1.121 | 1.292 | 1.172 |
| TBHP | 18.084 | 17.198 | 7.959 | 3.039 | 0.773 |

TABLE IV

CATALYTIC CONVERSION OF TERT-BUTYLHYDROPEROXIDE TO TERT-BUTYLALCOHOL

| Notebook Number | 7012-25-F | 7012-27-1 | 7012-27-2 | 7012-27-3 | 7012-27-4 |
|---|---|---|---|---|---|
| Catalyst | | .2% Pd, .08% Au on $Al_2O_3$ | | | |
| Catalyst (cc) | | 100 | 100 | 100 | 100 |
| Pressure (psig) | | 300 | 300 | 300 | 300 |
| Feed Rate (cc/Hr.) | | 200 | 200 | 200 | 200 |
| Temperature (°C.) | | 40 | 60 | 80 | 100 |
| Time on Stream (Hr) | | 4 | 4 | 4 | 4 |
| Space Vel. (cc/cc) | | 2.0 | 2.0 | 2.0 | 2.0 |
| TBHP Conversion (mol. %) | | 0.0 | 22.6 | 67.9 | 92.4 |
| IB Conversion (mol. %) | | 7.8 | 6.1 | 16.7 | 16.9 |
| Sel. Acetone (mol. %) | | n.d. | 5.2 | 9.1 | 15.7 |
| Sel. Methanol (mol. %) | | n.d. | 1.3 | 1.4 | 2.9 |
| Sel. TBA (mol. %) | | n.d. | 84.1 | 83.2 | 79.5 |
| Sel. DTBP (mol. %) | | n.d. | 10.7 | 7.7 | 4.8 |
| Composition | | | | | |
| Isobutane | 57.704 | 53.231 | 54.157 | 48.039 | 47.959 |
| MEOH/MF | 0.101 | 0.114 | 0.120 | 0.163 | 0.273 |
| Acetone | 1.128 | 1.223 | 1.264 | 1.849 | 2.821 |
| TBA | 21.338 | 24.306 | 28.374 | 41.215 | 44.881 |
| DTBP | 0.681 | 0.793 | 1.036 | 1.443 | 1.327 |
| TBHP | 18.084 | 19.310 | 13.996 | 5.799 | 1.383 |

TABLE V

CATALYTIC CONVERSION OF TERT-BUTYLHYDROPEROXIDE TO TERT-BUTYLALCOHOL

| Notebook Number | 6844-10-A | 6879-31-1 | 6879-31-2 | 6879-31-3 | 6879-31-4 |
|---|---|---|---|---|---|
| Catalyst | | .2% Pd, .08% Au on $Al_2O_3$ | | | |
| Catalyst (cc) | | 50 | 50 | 50 | 50 |
| Pressure (psig) | | 500 | 500 | 500 | 500 |
| Feed Rate (cc/Hr.) | | 25 | 25 | 25 | 25 |
| Temperature (°C.) | | 80 | 100 | 120 | 140 |
| Time on Stream (Hr) | | 4 | 4 | 4 | 4 |
| Space Vel. (cc/cc) | | 0.5 | 0.5 | 0.5 | 0.5 |
| TBHP Conversion (mol. %) | | 88.9 | 93.2 | 96.2 | 97.4 |
| Selectivity IC4= (mol. %) | | 0.0 | −0.0 | 0.0 | 0.1 |
| Sel. Acetone (mol. %) | | 9.7 | 11.6 | 13.9 | 14.0 |
| Sel. Methanol (mol. %) | | 1.9 | 2.6 | 3.3 | 2.9 |
| Sel. TBA (mol. %) | | 82.8 | 83.3 | 81.6 | 82.0 |
| Sel. DTBP (mol. %) | | 7.5 | 5.1 | 4.4 | 4.0 |
| Remarks | $H_2O$ Free | $H_2O$ Free | $H_2O$ Free | $H_2O$ Free | $H_2O$ Free |

TABLE V-continued

CATALYTIC CONVERSION OF TERT-BUTYLHYDROPEROXIDE TO TERT-BUTYLALCOHOL

| Notebook Number | 6844-10-A | 6879-31-1 | 6879-31-2 | 6879-31-3 | 6879-31-4 |
|---|---|---|---|---|---|
| | Basis | Basis | Basis | Basis | Basis |
| Composition | | | | | |
| IC4= | 0.001 | 0.001 | 0.000 | 0.002 | 0.007 |
| MEOH/MF | 0.016 | 0.128 | 0.183 | 0.229 | 0.208 |
| Acetone | 0.008 | 1.072 | 1.347 | 1.662 | 1.692 |
| TBA | 79.968 | 94.807 | 95.467 | 95.799 | 96.080 |
| DTBP | 0.055 | 1.085 | 0.787 | 0.718 | 0.663 |
| TBHP | 19.146 | 2.126 | 1.293 | 0.731 | 0.506 |

TABLE VI

CATALYTIC CONVERSION OF TERT-BUTYLHYDROPEROXIDE TO TERT-BUTYLALCOHOL

| Notebook Number | 6844-10-A | 6879-32-1 | 6879-32-2 | 6879-32-3 | 6879-32-4 |
|---|---|---|---|---|---|
| Catalyst | | .2% Pd, .08% Au on $Al_2O_3$ | | | |
| Catalyst (cc) | | 50 | 50 | 50 | 50 |
| Pressure (psig) | | 500 | 500 | 500 | 500 |
| Feed Rate (cc/Hr.) | | 50 | 50 | 50 | 50 |
| Temperature (°C.) | | 80 | 100 | 120 | 140 |
| Time on Stream (Hr) | | 4 | 4 | 4 | 4 |
| Space vel. (cc/cc) | | 1.0 | 1.0 | 1.0 | 1.0 |
| TBHP Conversion (mol. %) | | 78.0 | 88.7 | 93.6 | 97.0 |
| Selectivity IC4= (mol. %) | | −0.0 | 0.0 | 0.0 | 0.1 |
| Sel. Acetone (mol. %) | | 9.6 | 14.9 | 18.4 | 20.4 |
| Sel. Methanol (mol. %) | | 1.6 | 3.2 | 4.7 | 5.9 |
| Sel. TBA (mol. %) | | 83.0 | 80.3 | 78.1 | 77.0 |
| Sel. DTBP (mol. %) | | 7.4 | 4.7 | 3.5 | 2.7 |
| Remarks | $H_2O$ Free Basis | $H_2O$ Free Basis | $H_2O$ Free Basis | $H_2O$ Free Basis | $H_2O$ Free Basis |
| Composition | | | | | |
| IC4= | 0.001 | 0.000 | 0.001 | 0.002 | 0.010 |
| MEOH/MF | 0.016 | 0.103 | 0.212 | 0.317 | 0.404 |
| Acetone | 0.008 | 0.933 | 1.643 | 2.135 | 2.446 |
| TBA | 79.968 | 92.570 | 94.177 | 94.745 | 95.098 |
| DTBP | 0.055 | 0.952 | 0.706 | 0.560 | 0.457 |
| TBHP | 19.146 | 4.213 | 2.155 | 1.233 | 0.573 |

TABLE VII

CATALYTIC CONVERSION OF TERT-BUTYLHYDROPEROXIDE TO TERT-BUTYLALCOHOL

| Notebook Number | 6844-10-A | 6879-33-1 | 6879-33-2 | 6879-33-3 | 6879-33-4 |
|---|---|---|---|---|---|
| Catalyst | | .2% Pd, .08% Au on $Al_2O_3$ | | | |
| Catalyst (cc) | | 50 | 50 | 50 | 50 |
| Pressure (psig) | | 500 | 500 | 500 | 500 |
| Feed Rate (cc/Hr.) | | 100 | 100 | 100 | 100 |
| Temperature (°C.) | | 80 | 100 | 120 | 140 |
| Time on Stream (Hr) | | 4 | 4 | 4 | 4 |
| Space vel. (cc/cc) | | 2.0 | 2.0 | 2.0 | 2.0 |
| TBHP Conversion (mol. %) | | 45.0 | 85.7 | 94.5 | 96.9 |
| Selectivity IC4= (mol. %) | | −0.0 | 0.0 | 0.0 | 0.1 |
| Sel. Acetone (mol. %) | | 7.5 | 15.7 | 22.5 | 24.1 |
| Sel. Methanol (mol. %) | | 1.2 | 3.9 | 6.9 | 7.9 |
| Sel. TBA (mol. %) | | 82.9 | 79.9 | 74.8 | 73.7 |
| Sel. DTBP (mol. %) | | 9.6 | 4.4 | 2.7 | 2.1 |
| Remarks | $H_2O$ Free Basis | $H_2O$ Free Basis | $H_2O$ Free Basis | $H_2O$ Free Basis | $H_2O$ Free Basis |
| Composition | | | | | |
| IC4= | 0.001 | 0.000 | 0.001 | 0.006 | 0.013 |
| MEOH/MF | 0.016 | 0.053 | 0.245 | 0.461 | 0.539 |
| Acetone | 0.008 | 0.424 | 1.663 | 2.626 | 2.894 |
| TBA | 79.968 | 87.174 | 93.373 | 94.467 | 94.655 |
| DTBP | 0.055 | 0.726 | 0.644 | 0.458 | 0.376 |
| TBHP | 19.146 | 10.532 | 2.743 | 1.052 | 0.602 |

Having thus described our invention, what is claimed is:

1. In a method wherein a tertiary butyl hydroperoxide charge stock comprising an organic solvent solution of tertiary butyl hydroperoxide that contains from about 5 to about 30 wt. % of tertiary butyl hydroperoxide is brought into continuous contact with a catalytically effective amount of a pelleted hydroperoxide decomposition catalyst in a hydroperoxide decomposition reaction zone in liquid phase with agitation under hydroperoxide conversion conditions including a temperature within the range of about 25° to about 250° C., a space velocity of about 0.5 to 2 volumes of tertiary butyl hydroperoxide charge stock per volume of catalyst per hour and a pressure of about 0 to about 1,000 psig to convert said tertiary butyl hydroperoxide to decomposition products, principally tertiary butyl alcohol, the improvement which comprises:
  a) using, as said tertiary butyl hydroperoxide charge stock a solution of tertiary butyl hydroperoxide in a cosolvent mixture of about 50 to about 80 wt. % of isobutane with, correspondingly, about 50 to 20 wt. % of tertiary butyl alcohol,
  b) using an alumina-supported palladium/gold catalyst as said hydroperoxide decomposition catalyst, and
  c) recovering tertiary butyl alcohol from the products of said hydroperoxide decomposition reaction.

2. A method as in claim 1 wherein the temperature is in the range of about 40° to about 150° C. the space velocity is within the range of about of about 0.5 to 1 volumes of tertiary butyl hydroperoxide charge stock per volume of catalyst per hour and the pressure is about 0 psig.

3. A method as in claim 1 wherein the hydroperoxide decomposition catalyst consists essentially of alumina having deposited thereon from about 0.1 to about 1 wt. % of a mixture of palladium and gold supported on alumina.

4. A method as in claim 3 wherein the hydroperoxide decomposition catalyst consists essentially of alumina having deposited thereon about 0.2 wt. % of palladium and about 0.08 wt. % of gold.

* * * * *